(12) United States Patent
Mellenberg et al.

(10) Patent No.: US 9,795,805 B2
(45) Date of Patent: Oct. 24, 2017

(54) PROTON THERAPY MULTI-LEAF COLLIMATOR BEAM SHAPING

(71) Applicant: Varian Medican Systems, Inc., Palo Alto, CA (US)

(72) Inventors: Dave Mellenberg, Phoenix, AZ (US); Wolfgang Kaissl, Wil (CH); Jan Timmer, San Jose, CA (US)

(73) Assignees: Varian Medical Systems, Inc., Palo Alto, CA (US); Varian Medical Systems International AG, Cham (CH)

( * ) Notice: Subject to any disclaimer, the term of this patent is extended or adjusted under 35 U.S.C. 154(b) by 0 days.

(21) Appl. No.: 14/865,482

(22) Filed: Sep. 25, 2015

(65) Prior Publication Data

US 2017/0087386 A1  Mar. 30, 2017

(51) Int. Cl.
*A61N 5/10* (2006.01)

(52) U.S. Cl.
CPC .... *A61N 5/1045* (2013.01); *A61N 2005/1087* (2013.01)

(58) Field of Classification Search
CPC ......... A61N 5/1045; A61N 2005/1087; G21K 1/046
See application file for complete search history.

(56) References Cited

U.S. PATENT DOCUMENTS

| 5,351,280 | A * | 9/1994 | Swerdloff | A61N 5/1042 378/150 |
|---|---|---|---|---|
| 7,397,901 | B1 * | 7/2008 | Johnsen | G21K 1/04 378/147 |
| 7,555,103 | B2 * | 6/2009 | Johnsen | G21K 1/04 378/147 |
| 9,168,390 | B2 * | 10/2015 | Iwata | A61N 5/103 |
| 9,443,633 | B2 * | 9/2016 | Orton | G21K 1/046 |
| 2006/0198492 | A1 * | 9/2006 | Noguchi | G21K 1/04 378/15 |
| 2008/0267356 | A1 * | 10/2008 | Johnsen | G21K 1/04 378/152 |
| 2009/0041199 | A1 * | 2/2009 | Bohn | A61N 5/1042 378/152 |
| 2009/0173637 | A1 * | 7/2009 | Bourne | G21K 1/02 205/674 |
| 2010/0034357 | A1 * | 2/2010 | Svesson | A61N 5/1042 378/152 |
| 2014/0217312 | A1 * | 8/2014 | Echner | G21K 1/046 250/505.1 |
| 2015/0170778 | A1 * | 6/2015 | Echner | A61N 5/1045 250/505.1 |
| 2015/0273239 | A1 * | 10/2015 | Hsu | A61N 5/1045 378/150 |
| 2017/0106212 | A1 * | 4/2017 | Raleigh | A61N 5/1049 |

* cited by examiner

*Primary Examiner* — Wyatt Stoffa (57) ABSTRACT

System and method for shaping the intensity profile of a radiation beam incident on a target volume. Embodiments according to the present disclosure include a multi-leaf collimator (MLC) capable of sharpening (e.g., "trimming") a proton beam, the MLC having a reduced overall weight. Leaves of the MLC according to embodiments of the present disclosure have two regions of different density, where a high density region is proximal to a radiation beam so as to block a portion of the beam, and a lower density region provides structural integrity to the leaf while reducing overall MLC weight.

17 Claims, 8 Drawing Sheets

PROTON THERAPY MULTI-LEAF COLLIMATOR BEAM SHAPING

TECHNICAL FIELD

Embodiments of the invention relate generally to radiation shielding. More specifically, embodiments of the invention pertain to a multi-leaf collimator that can be used in applications such as radiotherapy.

BACKGROUND

In conventional radiotherapy a source of radiation is used to irradiate a tumor, while shielding may be provided for the areas surrounding the tumor in order to minimize irradiation of the non-tumor areas. The shielding may be a simple milled block of dense material, where a void is milled in the negative of the tumor shape, thus permitting a beam of radiation largely shaped like the tumor to pass through. Such approaches are both simple and somewhat effective in concentrating radiation at the site of the tumor, while sparing surrounding tissue.

In proton therapy the use of a milled block is often employed. Proton therapy is distinct from photon therapy (e.g., x-ray) in that proton therapy uses accelerated particles, where the energy of the particle (e.g., 70 MeV-250 MeV) is set to determine how deeply into a body the particle will penetrate. The particle, when absorbed, transfers its energy to the absorbing tissue. This method of therapy enables more directed treatment of tumors, as compared to x-ray radiation (which penetrates through the body, transferring energy along its path).

Proton therapy can be broadly categorized into two modalities. The first is scattering proton therapy, wherein a radiation source is emitted over a wide field with portions of the radiation beam selectively blocked, in order to focus the radiation onto the target area (e.g., a tumor). The second is so-called "pencil beam" proton therapy, wherein a finely focused proton beam is scanned across a tumor. Somewhat akin to a cathode-ray tube television, a pencil beam proton therapy is magnetically directed in order to "paint" a tumor, delivering a very precise dose. This scanning is typically done without the presence of any collimator or MLC.

Scattering proton therapy may use multi-leaf collimators (MLCs), which are commonly used in x-ray radiotherapy machines. Typically, an MLC includes two sets of independently adjustable leaves. Each leaf is thick enough to attenuate or block completely a beam of radiation. The leaves can be positioned independently of one another to form an aperture in a shape like that of the area to be irradiated, so that only the targeted area is irradiated while surrounding areas are shielded.

A radiotherapy session may include radiation delivery from several (e.g., 2-5) dose angles. Compared with x-ray radiation, the leaves of the MLC need to be larger (e.g., thicker) in order to direct, or block, a proton beam. This leads to increased weight of a proton beam MLC compared to an MLC used exclusively for x-ray radiotherapy, with corresponding greater difficulty in manipulating the collimators during treatment (e.g., swapping out collimators, or changing angles for multiple doses). In particular, the weight of a MLC designed for proton therapy restricts its use on a gantry. These proton therapy designs (e.g., those having thick, dense MLC leaves) also cost more and have greater inertia due to the MLC leaf weight.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Targeted delivery of radiation to specified areas of the body while sparing surrounding tissues is paramount for effective radiotherapy. According to embodiments of the present disclosure described herein, the beam intensity profile of a scanning proton beam, which is Gaussian in shape, can be sharpened along the edge of the profile in order to deliver even more precise doses to a tumor, especially delivery locations near vital organs. In order to sharpen the intensity profile of a scanning proton beam (e.g., pencil beam), only the edges need be removed. Therefore, embodiments according to the present disclosure provide an MLC capable of sharpening (e.g., "trimming") a proton beam, the MLC having a reduced overall weight. In one embodiment, the leaves of an MLC are reduced in dimension (for example, have an abbreviated length) compared to conventional MLC leaves. In one embodiment, the leaves of an MLC have two regions of different density, where a high density region is proximal to a radiation beam so as to block a portion of the beam, and a lower density region provides structural integrity to the leaf while reducing overall weight.

According to an embodiment of the present disclosure, a multi-leaf collimator includes a plurality of independently adjustable leaves. The multi-leaf collimator includes a first leaf, the first leaf including a first region and a second region adjacent to the first region. The first region is operable for blocking a portion of an incident beam of radiation passing proximal to the first region, with respect to the second region. The first region has a higher density than the second region, the second region providing structural support for the first leaf.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in a figure herein (e.g., FIG. 7) describing the operations of this method, such steps and sequencing are exemplary. Embodiments are well suited to performing various other steps or variations of the steps recited in the flowchart of the figure herein, and in a sequence other than that depicted and described herein.

Figure 1:
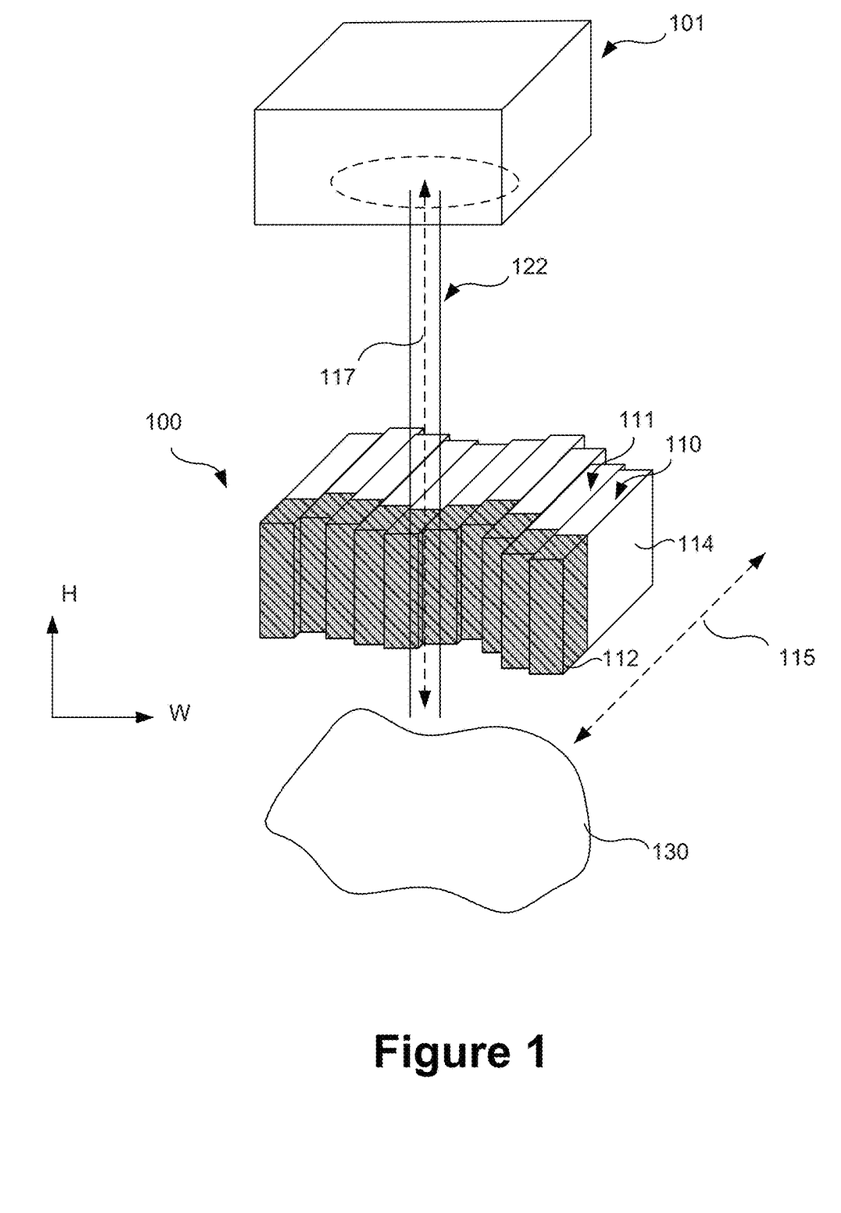
FIG. 1 is a perspective view of a portion of a multi-leaf collimator (MLC), in accordance with one embodiment of the present disclosure.

FIG. 1 is a perspective view of a portion of a multi-leaf collimator (MLC) 100 in accordance with one embodiment of the present disclosure. Generally speaking, MLC 100 is designed to define and restrict (constrict) the dimensions of a radiation beam 122. In one embodiment, MLC 100 is implemented as part of a radiotherapy machine. In one embodiment, radiation beam 122 is a beam of charged particles such as protons, electrons or heavy ions. In an embodiment, radiation beam 122 is a narrow, mono-energetic "pencil" beam of charged particles, scanned magnetically across a target volume. In one embodiment, radiation beam 122 is a beam of x-rays.

Figure 2:
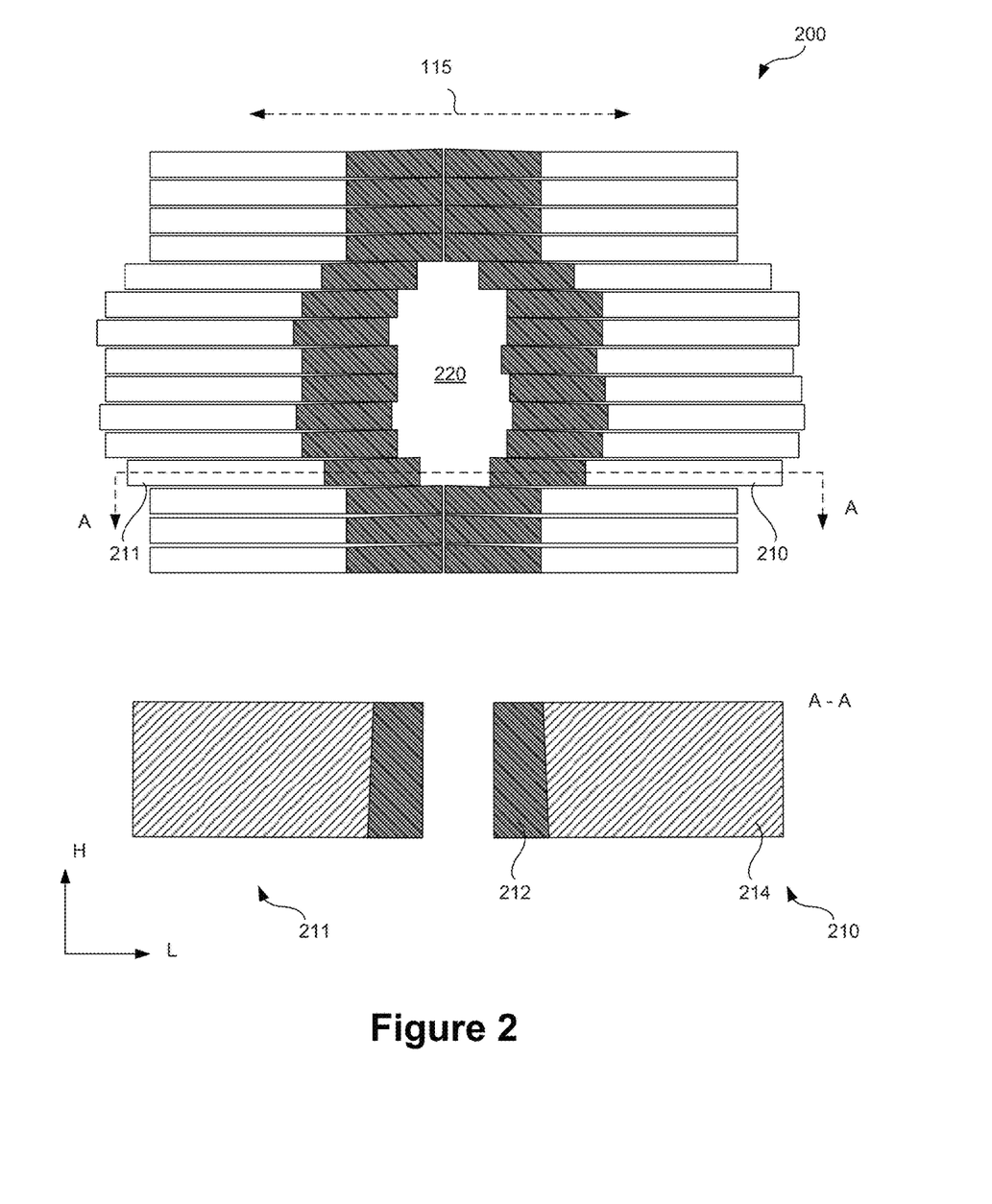
FIG. 2 is a top-down view of a portion of an MLC, including a cross-sectional view of adjacent leaves, in accordance with one embodiment of the present disclosure.

In the example of FIG. 1, MLC 100 includes a set of plates or leaves, exemplified by leaves 110 and 111. MLC 100 may include other components not illustrated or discussed herein, such as guides or tracks for the leaves, drive mechanisms, suspension mechanisms, and so on. As illustrated in FIG. 2, there may be a second set of leaves opposing the first set in a symmetrical or mirror-like fashion. In the examples of FIGS. 1 and 2, any leaf can be adjusted independently of any other leaf, along a translation axis 115. Leaves can be moved back and forth along the translation axis 115 in the directions indicated by the arrows.

With reference to FIG. 1, the MLC 100 is situated between a source 101 of the radiation beam 122 and a target volume 130. The radiation beam 122 propagates primarily in a direction along radiation beam axis 117. According to an embodiment of the present disclosure, leaf translation axis 115 is substantially perpendicular to radiation beam axis 117, such that translation of one or more leaves of MLC 100 serves to position the leaves to a greater or lesser extent within the radiation beam 122, and to thereby block at least a portion of radiation beam 122. In an embodiment, the leaves of the MLC 100 are positioned to shape, or trim (e.g., block only a portion of) the radiation beam 122. In an embodiment, the projected shape of the target volume 130— that is, the shape of the area to be exposed to the beam 122—is defined by positioning the leaves of the MLC 100 accordingly. The leaves block portions of the beam 122, while other portions of the beam reach the defined target volume 130 unblocked. Unless otherwise indicated, the word "block" is used herein in the general sense to mean either "prevent" (completely block) or "hinder" (partially block or attenuate). Thus, areas outside of the target volume 130 are shielded at least to some extent from the beam 122, so that areas outside the target volume are not exposed to unnecessary levels of radiation.

According to an embodiment, the leaves 110 and 111 are designed to have a reduced size and weight compared to conventional leaves of an MLC for operation in a scattering proton therapy application. For example, the length or thickness of leaves 110 and 111 can be reduced compared to leaves of an MLC for operation in a scattering proton therapy application. The leaves 110 and 111 can be all of one material. According to an embodiment, leaves 110 and 111 are designed with two regions 112 and 114, the regions 112 and 114 having different density. In the discussion herein, a higher density region of a leaf (e.g., region 112) may be referred to as the "first region" of a leaf, while the region of a leaf other than the high-density region (e.g., region 114) may be referred to as the "second region" of the leaf. According to embodiments of the present disclosure, the first region 112 is operable for trimming (e.g., blocking) at least a portion of radiation beam 122, while the second region 114 is for structural support of the leaf body. As used with reference to regions 112 and 114, density is the bulk density, that is, the density of the overall region (including any void spaces), and not strictly of the material(s) of which the leaves are constructed (the density of the leaf material is contributory to the overall density, of course). In some embodiments, density of region 114 is lower due to lower density material (e.g., low-Z material), and in some embodiments density of region 114 is reduced by voids formed within the body of the material in region 114. Region 112 typically is formed by a high-density (e.g., high-Z material).

The regions 112 and 114 each have a width (measured in the direction W of FIG. 1) and a height or thickness (measured in the direction H of FIG. 1). In a radiotherapy machine that uses charged particles, such as protons and heavy ions, the charged particles have a definite range in a given material. Accordingly, in a radiotherapy machine that uses charged particles, the region 112 can be made thick enough to completely block the charged particles. That is, the thickness of material used to form each of the region 112 meets or exceeds the range, at a given energy (e.g., 150 MeV), of charged particles in the material. In contrast to charged particles, x-rays will be attenuated as they pass through the region 112, in which case the region 112 and 114 can each be made thick enough to reduce the x-ray dosage by a desired amount. In operation, the radiation beam 122 of a radiotherapy device may be steered such that a proton beam is aimed precisely to be incident only at the region 112, such that region 114 is avoided. Therefore the radiation beam is partially blocked, or shaped, by the material within region 112, while the lower density of region 114 reduces the overall weight of the leaf 110. The regions 112 and 114 can describe adjacent regions of one leaf, that is, a contiguous leaf body can include regions 112 and 114. In an embodiment, the regions 112 and 114 together define the entirety of a leaf body. Each leaf in MLC 100 may be similarly designed.

Embodiments of the present disclosure include MLC designs operable in radiotherapy devices using fixed MLC configurations, as well as radiotherapy devices incorporating automated MLC leaf movement, under computer control (e.g., computer system 700). For example, the MLC movement can be coordinated with the rotation of the radiation beam about a patient (e.g., rotation via a gantry), such that multiple doses may be delivered in a single radiotherapy session.

According to embodiments of the present disclosure, the first region 112 is made of a material that is different from the material used to make region 114. In one embodiment, the first region 112 is made of a material (which may be referred to herein as the "first material") that has a higher density than the material (which may be referred to herein as the "second material") that makes up region 114. In another embodiment, the first region 112 is made of a material that has a higher atomic number (a higher-Z material) than the material that makes up region 114 (e.g., a lower-Z material). Higher density or higher-Z materials ("higher density/higher-Z materials") include, but are not limited to, tungsten, tungsten alloys, tantalum, tantalum alloys, lead or lead alloys, while lower density or lower-Z materials ("lower density/lower-Z materials") include, but are not limited to, steel (various steel alloys), brass, zinc or copper. Generally speaking, a higher density/higher-Z material may be a material that has a density of about 15 gm/cm$^3$ or greater.

In general, for each leaf of MLC 100, the volume of the low density region 114 is greater than the volume of the high density region 112. Thus, according to embodiments of the present disclosure, the majority of each leaf in MLC 100 is made using a lower density/lower-Z material, while a lesser portion of each leaf is made using a higher density/higher-Z material. Leaves formed of different materials in this manner provide a number of advantages compared to leaves formed only of either higher density/higher-Z material or lower density/lower-Z material.

For one, because the leaves of MLC 100 utilize a reduced amount of higher density/higher-Z material relative to conventional leaves formed only of higher density/higher-Z material, they will weigh less than conventional leaves. Because they are lighter, the leaves of MLC 100 are easier to move and so the mechanisms for positioning them can be less robust. Also, higher density/higher-Z material can be difficult to work with (e.g., machine), and so by reducing the amount of such material, the leaves of MLC 100 can be easier to fabricate than conventional leaves. In addition, higher density/higher-Z material can be more expensive, and so by reducing the amount of such material, the leaves of MLC 100 can cost less than conventional leaves.

For embodiments where regions 112 and 114 are composed of different materials (e.g., such as described in FIGS. 4-5), fabrication of the leaves in MLC 100 (e.g., leaves 110 and 111) entails attaching or bonding the higher density/higher-Z portion and the lower density/lower-Z portion. This can be achieved in a number of different ways, depending on the materials used. The portions may be joined using a technique such as brazing, for example. Alternatively, the portions may be joined mechanically (e.g., using screws or other types of fasteners).

FIG. 2 is a top-down view of a portion of an MLC 200 in accordance with one embodiment of the present disclosure. MLC 200 includes a number of leaves exemplified by leaves 210 and 211, which are also shown in cross-section along axis A-A. The leaves can be independently moved back and forth in the direction of arrow 115, in order to create an aperture 220 that defines the shape of a targeted area. Generally speaking, the leaves 210 and 211 lie on a common axis and move back and forth along that axis.

Continuing with reference to FIG. 2, the leaf 210 is designed with two regions 212 and 214, the regions 212 and 214 having different density. Each leaf in MLC 200 may be similarly designed. As before, according to embodiments of the present disclosure, the region 212 is operable for trimming (e.g., blocking) at least a portion of a radiation beam, while the region 214 is for structural support of the leaf body.

The regions 212 and 214 each have a height or thickness (measured in the direction H of FIG. 2). In a radiotherapy machine that uses charged particles, the region 212 can be made thick enough to completely block the charged particles. That is, the thickness of the region 212 can be chosen to meet or exceed the range of the charged particles in the material used to form those portions.

According to an embodiment of the present disclosure, the thickness H of the region 212 is designed to stop particles having an energy of approximately 150 MeV. For example, for copper the thickness can be approximately 25 mm; for brass the thickness can be approximately 25 mm; and for tungsten the thickness can be approximately 35 mm.

According to another embodiment of the present disclosure, the thickness H of the region 212 is designed to stop particles having an energy of approximately 250 MeV. For example, for copper the thickness can be approximately 50 mm; for brass the thickness can be approximately 50 mm; and for tungsten the thickness can be approximately 75 mm.

The region 212 is optimally as thin (in the L direction of FIG. 2) as practical, so as to provide blocking of radiation (e.g., sharpen the penumbra of a scanning proton beam), while the remainder of the leaf 210 is of lower density so as to reduce overall weight. As used herein, a penumbra of a radiation beam is a lateral penumbra, and corresponds to the spatial region of the radiation beam where the beam intensity is between 80% and 20% of the maximum intensity. In practice, the spatial extents of the lateral penumbra are influenced by the range of the radiation beam. The lateral extent can be approximately 3.5% of the range. For example, at a range of 10 cm, the penumbra will have a width of approximately 3.5 mm. According to embodiments of the present disclosure wherein the radiation beam is a scanning proton beam, region 212 can be between 10-20 cm along the L dimension, as a scanning proton beam is able to be steered very precisely to avoid the lower density region 214.

According to embodiments of the present disclosure, the region 212 is made of a material that is different from the material used to make the region 214. In one embodiment, the region 212 is made of a material (which may be referred to herein as the "first material") that has a higher density than the material (which may be referred to herein as the "second material") that makes up region 214. In another embodiment, the region 212 is made of a higher-Z material than the material that makes up region 214.

Thus, according to embodiments of the present disclosure, the bulk of each leaf in MLC 200 (that is, region 214) is made from a less dense/lower-Z material than the first region 212 of each leaf. Leaves formed of different materials in this manner provide a number of advantages compared to leaves formed entirely of either higher density/higher-Z material or lower density/lower-Z material. Those advantages have been previously discussed herein.

Figure 3:
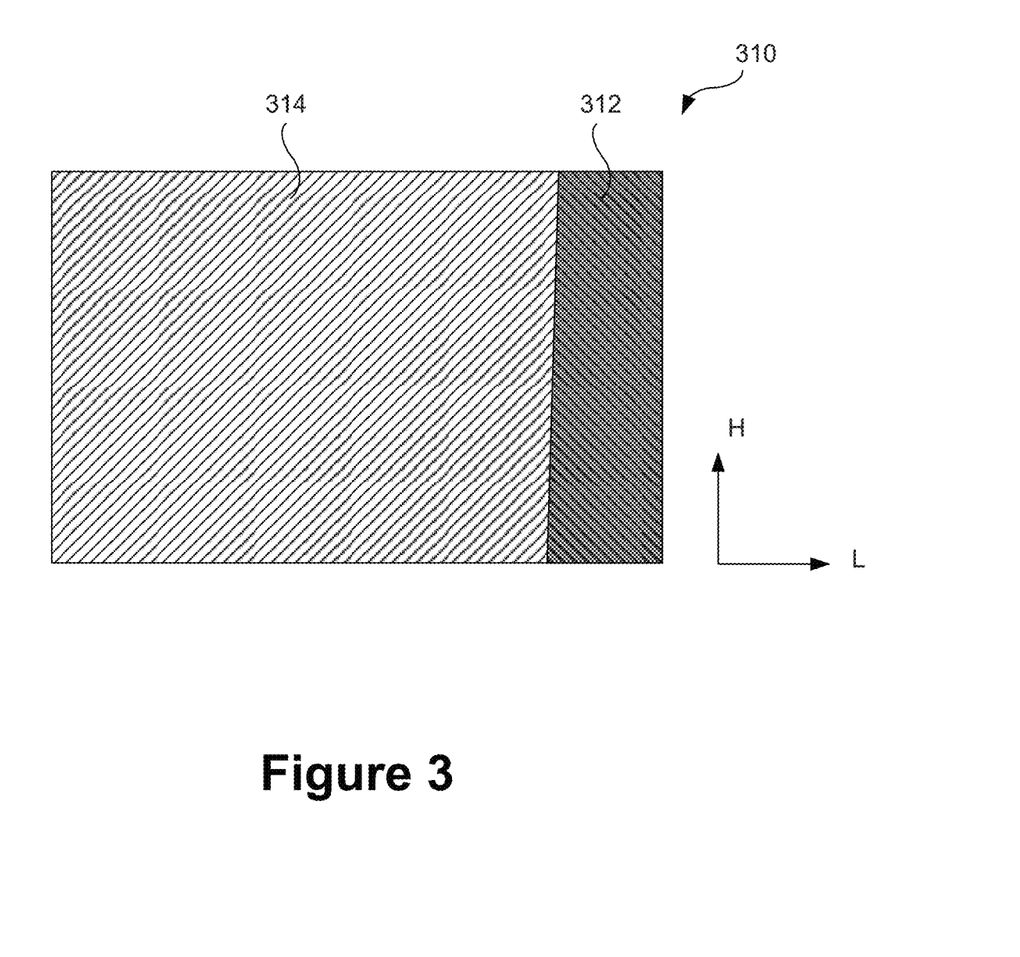
FIGS. 3-5 are cross-sectional views of adjacent leaves, in accordance with embodiments of the present disclosure.

FIG. 3 is a cross-sectional view of an MLC leaf 310 according to an embodiment of the present disclosure. Leaf 310 includes first region 312 and second region 314. According to the embodiment depicted in FIG. 3, the first region 312 is made of a material that is different from the material used to make second region 314. In one embodiment, the first region 312 is made of a material that has a higher density than the material that makes up second region 314. In another embodiment, the first region 312 is made of a higher-Z material than the material that makes up second region 314.

As mentioned above, lower density/lower-Z material is easier to work with than higher density/higher-Z material. Thus, an advantage associated with forming the second region 314 from lower density/lower-Z material is that the leaf 310 can be easier to machine. According to embodiments of the present disclosure, a leaf 310 may rely on the second region 314 to provide structural integrity to the overall leaf body, while the first region 312 serves to block radiation (e.g., scanning beam radiation). Therefore, the region 314 may be made from material with lesser density, such as lead or its alloys, than the material that makes up the first region 314 the leaf 310. This provides more flexibility in the design of the leaves.

Figure 4:
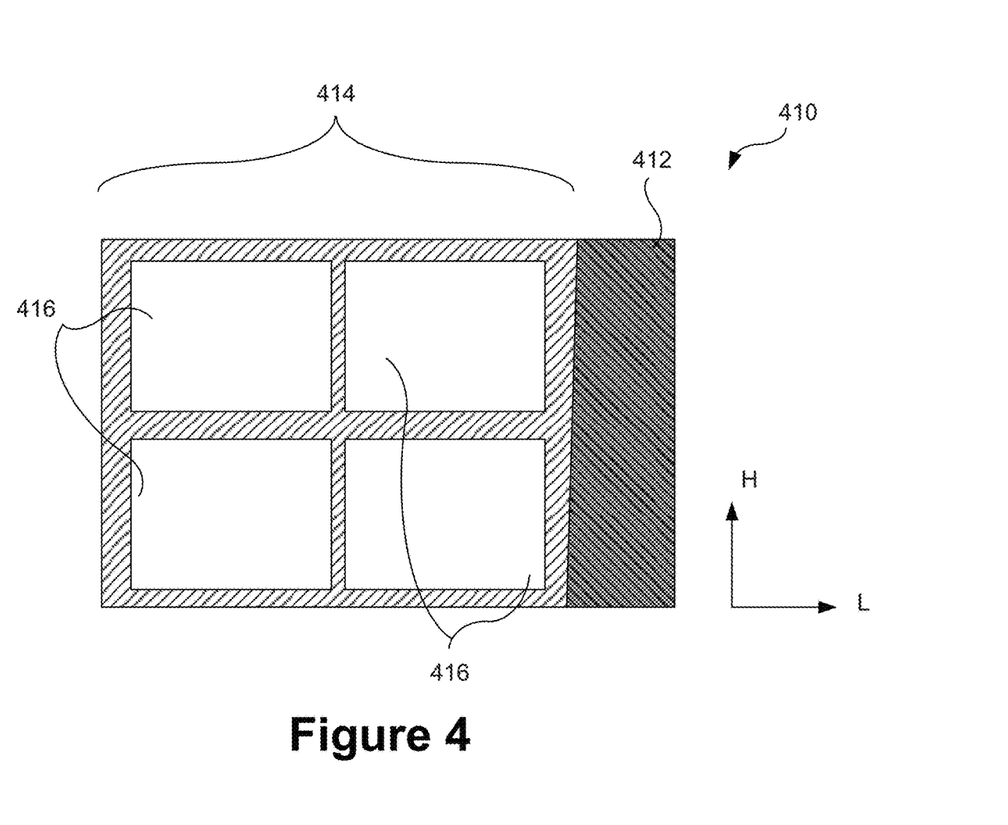

FIG. 4 illustrates a cross-sectional view of an MLC leaf according to another embodiment of the present disclosure. In the example of FIG. 4, leaf 410 is shown. Leaf 410 includes a region 412, and region 414. The region 412 may be referred to as the "first region" of leaf 410 and the region 414 may be collectively referred to as the "second region" of leaf 410. The second region 414 includes regions of voids 416, such that the overall density of region 414 is reduced. The voids 416, while reducing the overall density of the second region 414 of leaf 410, are designed such that the leaf 410 retains structural integrity and is able to translate during operation in order to selectively obstruct (e.g., block) at least a portion of a radiation beam (e.g., radiation beam 122). The first region 412 is made of a material that is different from the material used to make region 414. In one embodiment, the first region 412 is made of a material that has a higher density than the material that makes up region 414. In another embodiment, the first region 412 is made of a higher-Z material than the material that makes up region 414. In general, the total thickness (H) of the region 412 is sufficient to attenuate or completely block a radiation beam, e.g., a scanning proton beam.

While the voids 416 are depicted as rectangular in shape, other shapes (e.g., ovoid, square, triangular, etc.) are consistent with the spirit and scope of the present disclosure. Further, according to some embodiments of the present disclosure the region 414 may be used to shape a radiation beam (e.g., radiation beam 122), and the pattern of the voids 416 is designed according to the shaping requirement.

Figure 5:
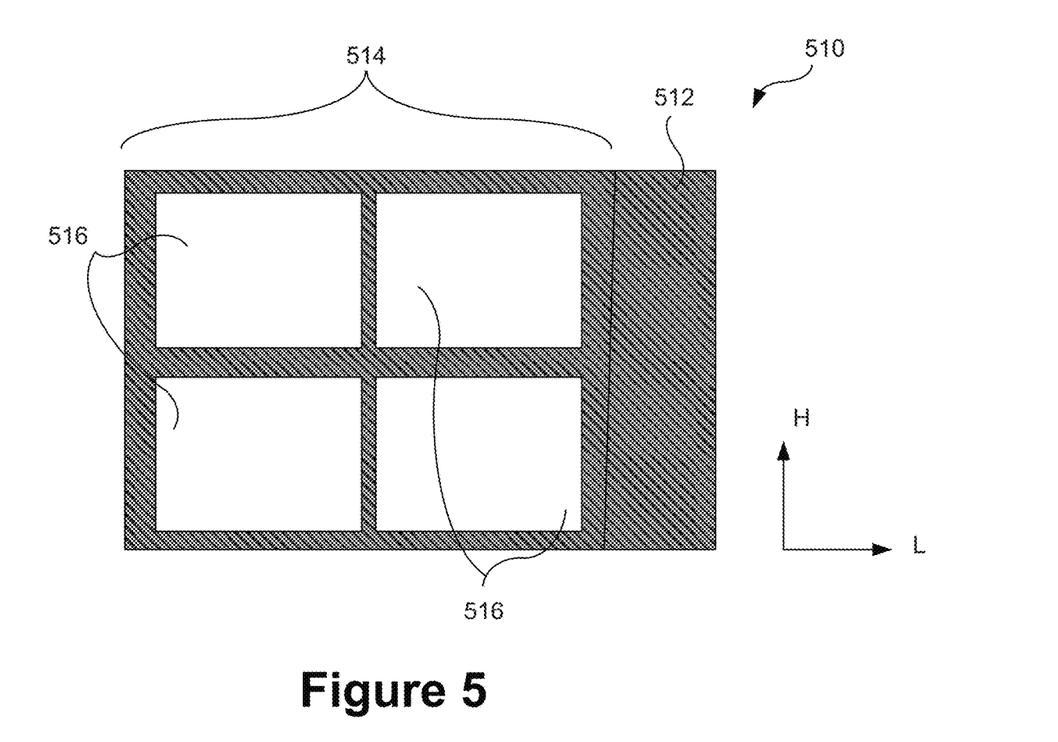

In the example of FIG. 5, a leaf 510 of an MLC is shown. Leaf 510 includes a region 512, and region 514. The region 512 may be referred to as the "first region" of leaf 510 and the region 514 may be collectively referred to as the "second region" of leaf 510. The second region 514 includes regions of voids 516, such that the overall density of region 514 is reduced. While the voids 516 are depicted as rectangular in shape, other shapes (e.g., ovoid, square, triangular, etc.) are consistent with the spirit and scope of the present disclosure. The voids 516, while reducing the overall density of the second region 514 of leaf 510, are designed such that the leaf 510 retains structural integrity and is able to translate during operation in order to selectively obstruct (e.g., block) at least a portion of a radiation beam (e.g., radiation beam 122). The first region 512 and second region 514 are made of the same material. In one embodiment, the regions 512 and 514 are made of a material that has a high density e.g., a high-Z material. In general, the total thickness (H) of the region 512 is sufficient to attenuate or completely block a radiation beam, e.g., a scanning proton beam.

Proton Therapy System

Figure 6:
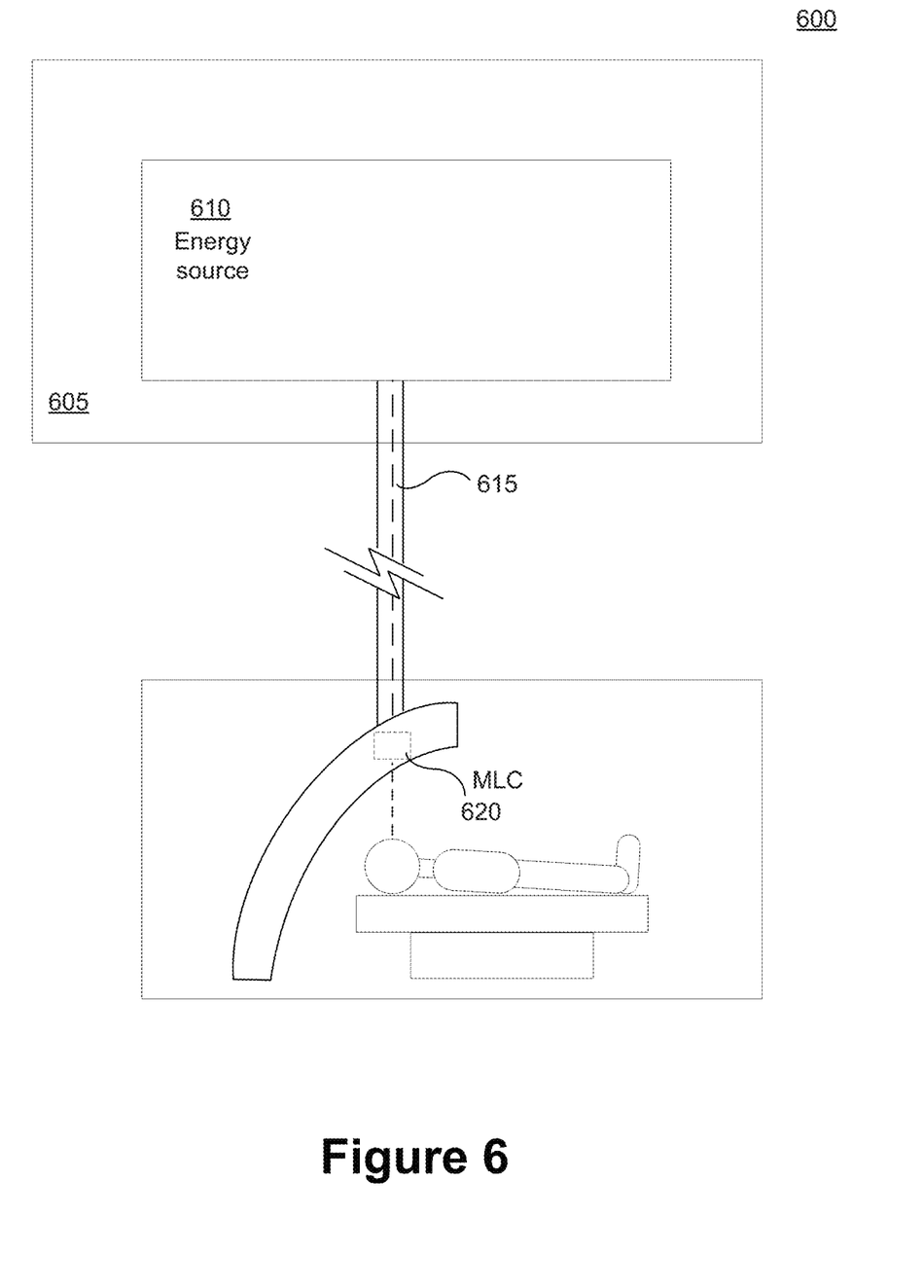
FIG. 6 is a schematic diagram of a proton therapy apparatus, in accordance with embodiments of the present disclosure.

FIG. 6 illustrates a schematic of a particle radiation system 600 for providing particle beams for particle therapy in accordance with embodiments of the present disclosure. The system 600 comprises a single energy source 610 (e.g., stationary cyclotron or synchrotron) located in a dedicated room 605. The energy source 610 is operable to generate a particle beam 615, for example, a proton beam. The particle beam 615 is produced with a specific level of energy that can be adjusted to a prescribed energy level by virtue of energy selection, and is then provided to a treatment station via a beam transportation system. The beam transport system can tune and deliver the particle beam to a radiation station. At the end of the beam transport system, a rotational gantry associated with a radiation nozzle is capable of delivering the beam onto an irradiation object, e.g. a tumor of a patient, in a fixed position supported by the irradiation station during operation. The radiation nozzle includes a multi-leaf collimator (MLC) 620 as described herein, where the MLC is operable to block a portion of the particle beam in order to sharpen the incident beam delivered to the patient tumor. The MLC is able to be under computer control, such that movements and positions of the leaves of the MLC are directed in order to sharpen the particle beam 615 for improved precision in radiation delivery to the patient tumor. Similar systems can be used for other heavy particle radiation treatment, such as neutron, He or C ion beam.

Figure 7:
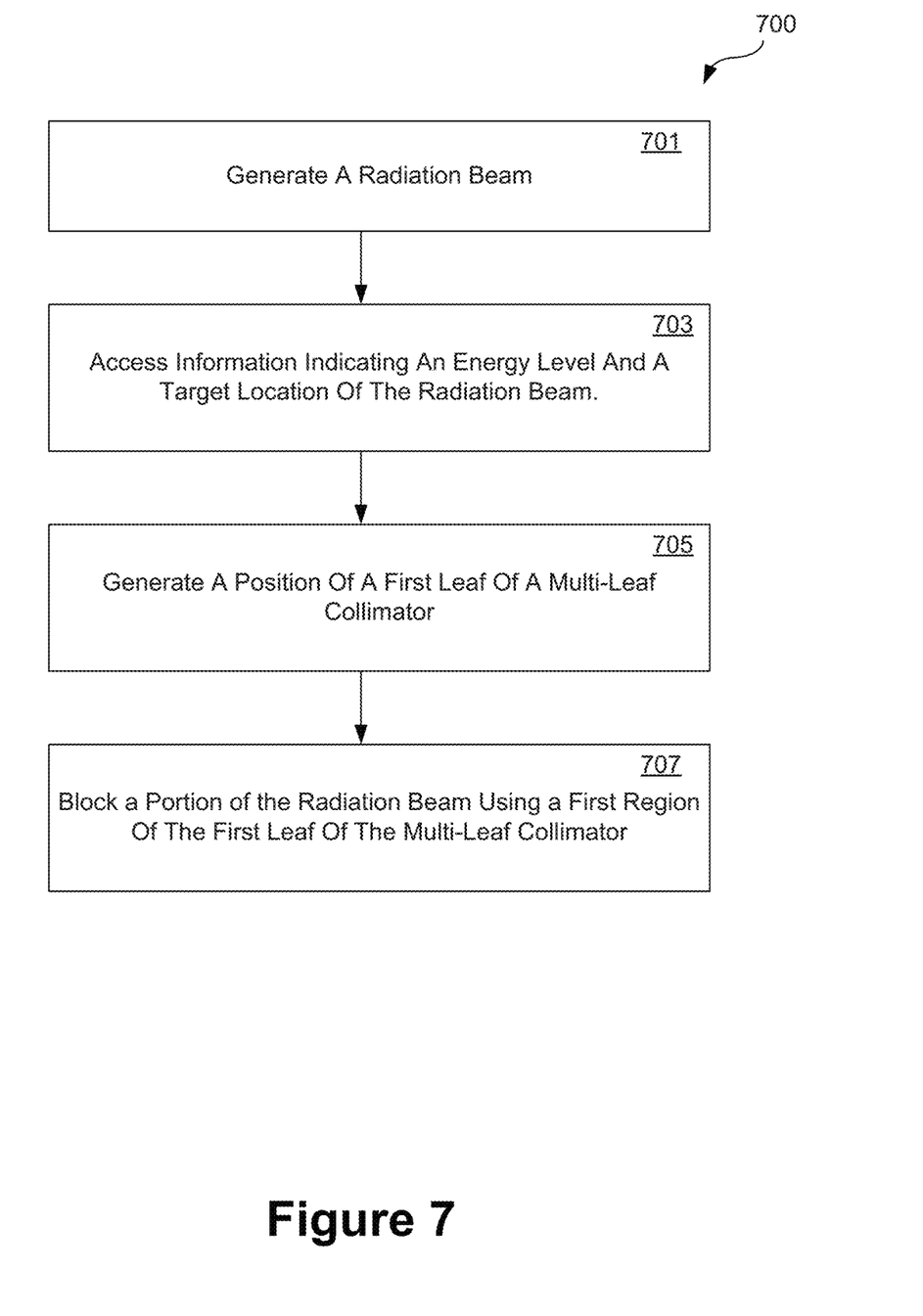
FIG. 7 is a flowchart of a method of shaping a beam of radiation, in accordance with one embodiment of the present disclosure.

FIG. 7 is a flowchart 700 of a method of shaping a beam of radiation according to an embodiment of the present invention. Although specific steps are disclosed in flowchart 700, such steps are exemplary. That is, the present invention is well-suited to performing various other steps or variations of the steps recited in flowchart 700. According to embodiments of the present disclosure, the method 700 can be implemented by a computing system, for example, computing system 800.

In step 701, a radiation beam is generated. In an embodiment, the radiation beam is a particle beam, for example a proton pencil beam. In an embodiment, the radiation beam is scanned across a target volume of a patient. The radiation beam is able to be generated at different energies, for example, 150 MeV-250 MeV. The energy of the radiation beam can be selected according to a target penetration depth at which to provide radiotherapy to a target volume.

In step 703 an access is made of information indicating an energy level and a target location of the radiation beam generated in step 701. The target location, along with the energy level, provides information on an expected position and intensity profile for the incident radiation beam. In step 705 a position of a first leaf of a multi-leaf collimator (e.g., MLC 200) is generated. The position generated may be based on the information accessed in step 703.

In step 707 a portion of the radiation beam is blocked using a first region (e.g., region 212) of a leaf of a multi-leaf collimator (e.g., MLC 200). The leaves of the MLC each contain two regions of different density, where the region of higher density is proximal to the radiation beam, and the region of lower density provides structural integrity to the leaf while reducing the overall weight of the leaf. The blocking can be partial blocking (e.g., trimming) of a radiation beam of protons, such as a scanning proton beam. The partial blocking is able to be a portion of the penumbra of the radiation beam, where the lateral extents of the penumbra depend upon the spot size of the radiation beam and the radiation beam energy (e.g., the energy determines the range of penetration for a particle beam, for example depth in a target volume). In this manner a penumbra of a particle beam may be "sharpened," enabling increased discrimination in dose delivery to a target volume while sparing healthy surrounding tissue.

The process 700 is able to include further steps. A position of the leaf is able to be changed, for example. The change in position can be in order to provide a radiation dose to a patient at a different angle than the first dose, or any other dose. According to embodiments of the present disclosure, the change in position is automatic, and is based on a location of a treatment volume in a patient and a number of dose angles comprising a complete treatment session of the patient.

At a first or subsequent dose angle, a portion of the radiation beam is blocked using the first region of any leaf of the MLC. According to an embodiment, the radiation beam is a scanning proton beam continuously scanned across the treatment volume, and the blocking is of a penumbra of the scanned proton beam. According to an embodiment of the present disclosure, the radiation beam is disabled while a dose angle is changing, and enabled when the selected dose angle is achieved and the positions of one or more leaves of the MLC are configured for the current dose angle.

Exemplary Computing Device

Figure 8:
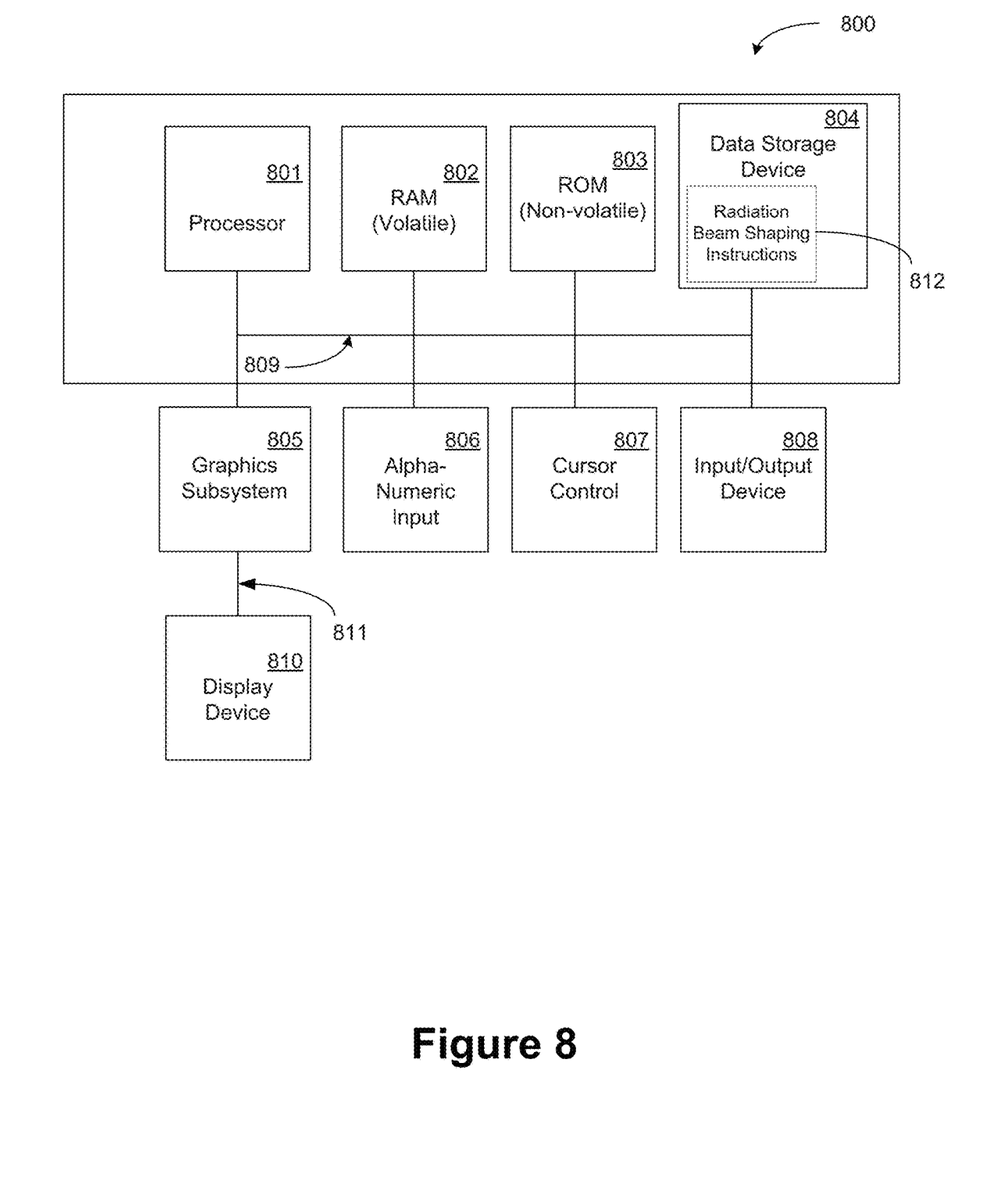
FIG. 8 is an exemplary computing environment, in accordance with one embodiment of the present disclosure.

As presented in FIG. 8, an exemplary system upon which embodiments of the present invention may be implemented includes a general purpose computing system environment, such as computing system 800. In its most basic configuration, computing system 800 typically includes at least one processing unit 801 and memory, and an address/data bus 809 (or other interface) for communicating information. Depending on the exact configuration and type of computing system environment, memory may be volatile (such as RAM 802), non-volatile (such as ROM 803, flash memory, etc.) or some combination of the two.

Computer system 800 may also comprise an optional graphics subsystem 805 for presenting information to the computer user, e.g., by displaying information on an attached display device 810, connected by a video cable 811. According to embodiments of the present claimed invention, the graphics subsystem 805 may be coupled directly to the display device 810 through the video cable 811. A graphical user interface of an application for controlling a medical radiotherapy device including multi-leaf collimator, executing in the computer system 800, may be generated in the graphics subsystem 805, for example, and displayed to the user in the display device 810. In alternate embodiments, display device 810 may be integrated into the computing system (e.g., a laptop or netbook display panel) and will not require a video cable 811.

Additionally, computing system 800 may also have additional features/functionality. For example, computing system 800 may also include additional storage (removable and/or non-removable) including, but not limited to, magnetic or optical disks or tape. Such additional storage is illustrated in FIG. 8 by data storage device 804. Computer storage media includes volatile and nonvolatile, removable and non-removable media implemented in any method or technology for storage of information such as computer readable instructions, data structures, program modules or other data. RAM 802, ROM 803, and data storage device 804 are all examples of computer storage media. According to embodiments of the present disclosure, data storage device 804 includes radiation beam shaping instructions 812, which are instructions which cause computing system 800 to perform processes according to the disclosure herein (e.g., process 700).

Computer system 800 also comprises an optional alphanumeric input device 806, an optional cursor control or directing device 807, and one or more signal communication interfaces (input/output devices, e.g., a network interface card) 809. Optional alphanumeric input device 806 can communicate information and command selections to central processor 801. Optional cursor control or directing device 807 is coupled to bus 809 for communicating user input information and command selections to central processor 801. Signal communication interface (input/output device) 809, also coupled to bus 809, can be a serial port. Communication interface 809 may also include wireless communication mechanisms. Using communication interface 809, computer system 800 can be communicatively coupled to other computer systems over a communication network such as the Internet or an intranet (e.g., a local area network), or can receive data (e.g., a digital television signal).

In summary, according to embodiments of the present invention, the leaves of an MLC can be fabricated to contain regions of differing density. The regions together may include a combination of materials, or they may be all of the same material. Specifically, a higher density/higher-Z material can be used in a region of each leaf that is proximal to a radiation beam, for example, a scanning proton beam, in order to block at least a portion of the radiation beam. The remainder of each leaf has a lower density, either by being made of a lower density/lower-Z material, by including void regions, or a combination of these. Such leaves can be lighter, less expensive, and easier to fabricate.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments described herein were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation therapy apparatus comprising:
a multi-leaf collimator disposed between a source and a target, said source operable for generating a radiation beam onto said target along a radiation beam axis, said multi-leaf collimator operable to selectively block at least a portion of said radiation beam to said target, wherein said collimator comprises a plurality of leaves configured for independent translation along a shared axis; said plurality of leaves including a first leaf having a first region and a second region having adjoining surfaces, wherein said first region also has a surface that faces toward said source and a surface that faces toward said target and is opposite said surface that faces toward said source, wherein said first region has a higher density than said second region and wherein said first region is proximal to said radiation beam axis, wherein further said adjoining surfaces of said first region and said second region are at an angle relative to said radiation beam axis such that an edge of said surface that faces toward said target is longer than an edge of said surface that faces toward said source.

2. The apparatus of claim 1 wherein said radiation beam comprises a proton beam, and wherein said portion comprises a portion of a lateral penumbra.

3. The apparatus of claim 1 wherein said first region and said second region comprise the same material, and wherein said second region further comprises a void region.

4. The apparatus of claim 1 wherein said first region comprises a first material and said second region comprises a second material different from said first material.

5. The apparatus of claim 4 wherein said first material is a higher density material and said second material is a lower density material.

6. The apparatus of claim 4 wherein said first material is a higher-Z material and said second material is a lower-Z material.

7. The apparatus of claim 4 wherein said first material is selected from the group consisting of: tungsten, tungsten alloys, tantalum, tantalum alloys, lead, and lead alloys.

8. The apparatus of claim 4 wherein said second material is selected from the group consisting of: steel, brass, zinc, and copper.

9. A method of shaping an incident beam of particle radiation, said method comprising:
accessing information indicating an energy level and a target location of said beam onto a target;
generating a position of a first leaf in a multi-leaf collimator based on said information, wherein said first leaf comprises a first region and a second region having adjoining surfaces, said first region having a density that is greater than a density of said second region, wherein said first region also has a surface that faces toward said incident beam and a surface that faces toward said target and is opposite said surface that faces toward said incident beam, wherein further said adjoining surfaces of said first region and said second region are at a non-zero angle relative to said incident beam such that an edge of said surface of said first region that faces toward said target is longer than an edge of said surface of said first region that faces toward said source; and
blocking a portion of said beam at said position using said first leaf.

10. The method of claim 9 wherein said particle beam comprises a proton beam, and wherein said portion comprises a portion of a lateral penumbra.

11. The method of claim 10 wherein the energy level of said proton beam is adjustable during a treatment of said target.

12. The method of claim 9 wherein said first region and said second region comprise the same material, and wherein said second region further comprises a void region.

13. The method of claim 9 wherein said first region comprises a first material and said second region comprises a second material different from said first material.

14. The method of claim 13 wherein said first material is a higher density material and said second material is a lower density material.

15. The method of claim 13 wherein said first material is a higher-Z material and said second material is a lower-Z material.

16. The method of claim 13 wherein said first material is selected from the group consisting of: tungsten, tungsten alloys, tantalum, tantalum alloys, lead, and lead alloys.

17. The method of claim 13 wherein said second material is selected from the group consisting of: steel, brass, zinc, and copper.

* * * * *